US006939956B2

(12) United States Patent
Lee et al.

(10) Patent No.: US 6,939,956 B2
(45) Date of Patent: Sep. 6, 2005

(54) VARIABLE REGION OF THE MONOCLONAL ANTIBODY AGAINST HBV S-SURFACE ANTIGEN AND A GENE ENCODING THE SAME

(75) Inventors: Jong Wook Lee, Kwacheon-Si (KR); In Young Ko, Anyang-Si (KR); Heui Keun Kang, Uiwang-Si (KR); Moo Young Song, Suwon-Si (KR); Tae Hun Song, Suwon-Si (KR); Chang Seok Kim, Suwon-Si (KR)

(73) Assignee: Yuhan Corporation (KR)

( * ) Notice: Subject to any disclaimer, the term of this patent is extended or adjusted under 35 U.S.C. 154(b) by 401 days.

(21) Appl. No.: 10/146,305

(22) Filed: May 15, 2002

(65) Prior Publication Data

US 2002/0173035 A1 Nov. 21, 2002

(30) Foreign Application Priority Data

May 16, 2001 (KR) ........................... 2001-26634

(51) Int. Cl.⁷ .................. C07H 21/04; C12N 15/00
(52) U.S. Cl. ............ 536/23.53; 435/69.6; 435/320.1
(58) Field of Search ................ 536/23.53; 530/387.1, 530/387.3, 388.1, 388.3; 424/130.1, 133.1, 141.1, 147.1; 435/69.6

(56) References Cited

FOREIGN PATENT DOCUMENTS

KR            10-0250832          2/1999

OTHER PUBLICATIONS

Chothia et al. J. Mol. Biol. 196:901–917, 1987.*
Rudikoff et al. Proc. Natl. Acad. Sci. USA, 79:1979–1983, 1982.*
Kim et al. Biotechnology and Bioengineering, 58(1):73–84, 1998.*

* cited by examiner

*Primary Examiner*—Larry R. Helms
*Assistant Examiner*—David J. Blanchard
(74) *Attorney, Agent, or Firm*—Cantor Colburn LLP

(57) ABSTRACT

The present invention relates to a variable region of the monoclonal antibody against the S-surface antigen of hepatitis B virus and a gene encoding the same, a recombinant vector containing the gene, and a transformant obtained from the recombinant vector.

10 Claims, No Drawings

SEQUENCE LISTING

<160> NUMBER OF SEQ ID NOS: 14

<210> SEQ ID NO 1
<211> LENGTH: 37
<212> TYPE: DNA
<213> ORGANISM: Artificial Sequence
<220> FEATURE:
<223> OTHER INFORMATION: primer

<400> SEQUENCE: 1
actagtagac atggtcctca tgttgctgct gctatgg        37

<210> SEQ ID NO 2
<211> LENGTH: 30
<212> TYPE: DNA
<213> ORGANISM: Artificial Sequence
<220> FEATURE:
<223> OTHER INFORMATION: primer -continued

```
<400> SEQUENCE: 2
cccaagctta ctggatggtg ggaagatgga                                      30

<210> SEQ ID NO 3
<211> LENGTH: 35
<212> TYPE: DNA
<213> ORGANISM: Artificial Sequence
<220> FEATURE:
<223> OTHER INFORMATION: primer

<400> SEQUENCE: 3
actagtcgac atgggatgga gcgggtctt tatct                                 35

<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4
cccaagcttc cagggggcaa gggatagacg gatgg                                35

<210> SEQ ID NO 5
<211> LENGTH: 390
<212> TYPE: DNA
<213> ORGANISM: Escherichia coli

<400> SEQUENCE: 5
gacattgtga tgtcacagtc tccatcctcc ctagctgtgt cagttggaga gaaggttact     60
atgagctgca gtccagtca gagcctttta tatagtggca atcaaaagaa ctacttggcc    120
tggtaccagc agaaaccagg gcagtctcct gaactgctga tttactgggc atccactagg    180
gaatctgggg tccctgatcg cttcacaggc agtggatctg gacagatttt cactctcacc    240
atcagcagtg tgaaggctga agacctggca gtttattact gtcagcaata ttatagctat    300
cggacgttcg gtggaggcac caagctggaa atcaaacggg ctgatgctgc accaactgta    360
tccatcttcc caccatccag taagcttggg                                     390

<210> SEQ ID NO 6
<211> LENGTH: 414
<212> TYPE: DNA
<213> ORGANISM: Escherichia coli

<400> SEQUENCE: 6
caggtccagc tgcagcagtc tggaactgag atggtaaggc ctggacttc agtcaaggtg      60 tcctgcaagg cttccggata ccccttcact aatcacttga tagagtgggt aaagcagagg    120
cctggacagg gccctgagtg gattggagtg attaatcctg gaagtggtgg tactaactac    180
aatgagaagt tcaagggcaa ggcaacactg actgcagaca atcctccag taccgcctac    240 atgcaactca acagcctgac atctgatgac tctgcggtct atttctgtgc aataatgaca    300
acatttttag gtgagggcta tgctatggac tactggggtc aaggaacctc agtcaccgtc    360
tcctcagcca aaacaacagc cccatccgtc tatcccttgg cccctggaag cttg          414

<210> SEQ ID NO 7
<211> LENGTH: 130
<212> TYPE: PRT
<213> ORGANISM: Escherichia coli
```

-continued

```
<400> SEQUENCE: 7

Asp Ile Val Met Ser Gln Ser Pro Ser Ser Leu Ala Val Ser Val Gly
  1               5                  10                  15

Glu Lys Val Thr Met Ser Cys Lys Ser Ser Gln Ser Leu Leu Tyr Ser
                 20                  25                  30

Gly Asn Gln Lys Asn Tyr Leu Ala Trp Tyr Gln Gln Lys Pro Gly Gln
             35                  40                  45

Ser Pro Glu Leu Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Ser Tyr Arg Thr Phe Gly Gly Gly Thr Lys Leu Glu Ile Lys
                100                 105                 110

Arg Ala Asp Ala Ala Pro Thr Val Ser Ile Phe Pro Pro Ser Ser Lys
            115                 120                 125

Leu Gly
    130

<210> SEQ ID NO 8
<211> LENGTH: 138
<212> TYPE: PRT
<213> ORGANISM: Escherichia coli

<400> SEQUENCE: 8

Gln Val Gln Leu Gln Gln Ser Gly Thr Glu Met Val Arg Pro Gly Thr
  1               5                  10                  15

Ser Val Lys Val Ser Cys Lys Ala Ser Gly Tyr Pro Phe Thr Asn His
                 20                  25                  30

Leu Ile Glu Trp Val Lys Gln Arg Pro Gly Gln Gly Pro Glu Trp Ile
             35                  40                  45

Gly Val Ile Asn Pro Gly Ser Gly Gly Thr Asn Tyr Asn Glu Lys Phe
     50                  55                  60

Lys Gly Lys Ala Thr Leu Thr Ala Asp Lys Ser Ser Ser Thr Ala Tyr
 65                  70                  75                  80

Met Gln Leu Asn Ser Leu Thr Ser Asp Asp Ser Ala Val Tyr Phe Cys
                 85                  90                  95

Ala Ile Met Thr Thr Phe Leu Gly Glu Gly Tyr Ala Met Asp Tyr Trp
                100                 105                 110

Gly Gln Gly Thr Ser Val Thr Val Ser Ser Ala Lys Thr Thr Ala Pro
            115                 120                 125

Ser Val Tyr Pro Leu Ala Pro Gly Ser Leu
    130                 135

<210> SEQ ID NO 9
<211> LENGTH: 17
<212> TYPE: PRT
<213> ORGANISM: Escherichia coli

<400> SEQUENCE: 9

Lys Ser Ser Gln Ser Leu Leu Tyr Ser Gly Asn Gln Lys Asn Tyr Leu
  1               5                  10                  15

Ala
```

-continued

```
<210> SEQ ID NO 10
<211> LENGTH: 7
<212> TYPE: PRT
<213> ORGANISM: Escherichia coli

<400> SEQUENCE: 10

Trp Ala Ser Thr Arg Glu Ser
 1               5

<210> SEQ ID NO 11
<211> LENGTH: 8
<212> TYPE: PRT
<213> ORGANISM: Escherichia coli

<400> SEQUENCE: 11

Gln Gln Tyr Tyr Ser Tyr Arg Thr
 1               5

<210> SEQ ID NO 12
<211> LENGTH: 5
<212> TYPE: PRT
<213> ORGANISM: Escherichia coli

<400> SEQUENCE: 12

Asn His Leu Ile Glu
 1               5

<210> SEQ ID NO 13
<211> LENGTH: 17
<212> TYPE: PRT
<213> ORGANISM: Escherichia coli

<400> SEQUENCE: 13

Val Ile Asn Pro Gly Ser Gly Gly Thr Asn Tyr Asn Glu Lys Phe Lys
 1               5                  10                  15
Gly

<210> SEQ ID NO 14
<211> LENGTH: 13
<212> TYPE: PRT
<213> ORGANISM: Escherichia coli

<400> SEQUENCE: 14

Met Thr Thr Phe Leu Gly Glu Gly Tyr Ala Met Asp Tyr
 1               5                  10
```

VARIABLE REGION OF THE MONOCLONAL ANTIBODY AGAINST HBV S-SURFACE ANTIGEN AND A GENE ENCODING THE SAME

TECHNICAL FIELD

The present invention relates to a variable region of the monoclonal antibody against the S-surface antigen of hepatitis B virus and a gene encoding the same, a recombinant vector containing the said gene, and a transformant obtained from the said recombinant vector.

BACKGROUND ART

Hepatitis B virus (hereinafter, referred to as "HBV"), known as the Dane particle, has a spherical feature of 42 nm diameter. The outer envelope contains a large amount of hepatitis B surface antigens and surrounds the inner nucleocapsid composed of 180 hepatitis B core proteins. The nucleocapsid contains HBV genome, polymerase, etc (Summers et al., Proc. Nat. Acad. Sci, 72, 4579, 1975; Pierre Tiollais et al., Science, 213, 406–411, 1981).

Within the HBV genome, the coding region of HBV surface antigens contains three open reading frame start sites which share a common termination codon producing same S domain. Thus, the HBV surface antigens may be classified into three types, i.e., (1) Small HBV Surface Antigen (hereinafter, referred to as "S-surface antigen"), containing only the S domain, (2) Middle HBV Surface Antigen (hereinafter, referred to as "M-surface antigen"), containing the S domain and an additional 55 amino acid domain known as Pre-S2, and (3) Large HBV Surface Antigen (hereinafter, referred to as "L-surface antigen"), containing the Pre-S1 domain as well as the Pre-S2 and S domain. Among the expressed surface antigens, S-surface antigen is about 80% or more.

Subtypes of S-surface antigen were classified according to their properties of antibody recognition. Antigenic domains expressed in all surface antigen were classified as determinant a. The four other subtypes are d or y and w or r. Determinant d has a lysine at residue 122 while y has arginine. Similarly, determinant w has a lysine at residue 160 while r has arginine (Kennedy R. C. et al., J. Immunol. 130, 385, 1983). Thus, serological types can be classified into four subtypes, such as adr, adw, ayr and ayw (Peterson et al., J. Biol. Chem. 257, 10414, 1982; Lars O. Marnius et al., Intervirology, 38, 24–34, 1995).

The S-surface antigen specifically binds to hepatocyte (Leenders et al., Hepatology, 12, 141, 1990; Irina Ionescu-Matiu et al., J. Med. Virology, 6, 175–178, 1980; Swan N. T. et al., Gastroenterology 80, 260–264, 1981; Swan N. T. et al., Gastroenterology, 85, 466–468, 1983; Marie, L. M. et al., Proc. Nat. Acad. Sci. 81, 7708–7712, 1984). And, it has been identified that human hepatic plasma membrane contains target proteins such as apolipoprotein H and endonexin II which specifically bind to S-surface antigen (Mehdi H. et al., J. Virol., 68, 2415, 1994.; Hertogs K. et al., Virology, 197, 265, 1993).

Meanwhile, in developing a useful therapeutic monoclonal antibody, a humanized antibody is preferable because monoclonal antibodies obtained from mice could cause an immune response when applying to human.

The Korean patent publication No. 1999-8650 has recently disclosed a variable region of the monoclonal antibody against a Pre-S1 epitope which solely exists in a L-surface antigen among the three HBV surface antigens (S-, M-, and L-surface antigens), a gene encoding the same, and a humanized antibody using the same. Because the L-surface antigen is only 1~2% of the expressed surface antigens, however, the L-surface antigen is inappropriate as a target for anti-HBV antibody development for diagnostic as well as therapeutic purposes.

DISCLOSURE OF THE INVENTION

Accordingly, a primary object of the present invention is to provide a gene encoding the variable region of a monoclonal antibody, specifically recognizing the S-surface antigen, especially determinant a, which commonly exists in all of the HBV surface antigens.

It is another object of the present invention to provide a recombinant vector comprising the above gene.

It is a further object of the present invention to provide a transformant obtained using the above recombinant vector.

It is still another object of the present invention to provide a variable region of the above monoclonal antibody.

In accordance with one aspect of the present invention, provided is a gene encoding the monoclonal antibody variable region which specifically recognizes the HBV S-surface antigen.

The present inventors immunize mice with the determinant adr type of S-surface antigen (International Enzymes Inc., USA) which is most frequently found in Korean HBV patients. The spleen cells obtained from the immunized mice were fused with myeloma cells ($SP_2O$—Ag14, ATCC CRL-1581) to generate a large number of hybridoma cells which, following subsequent cloning and selection procedures, eventually give rise to numerous monoclonal antibodies. The present inventors selected monoclonal antibodies specifically binding to the determinant a among the numerous monoclonal antibodies; and as a result, obtained a hybridoma cell line (mC6-9-1) producing a distinct monoclonal antibody which specifically binds to the determinant a with high binding affinity.

The present inventors isolated total RNAs from the said hybridoma cell line to synthesize the cDNAs of light and heavy chains, and finally, obtained about 440 bp of light chain cDNA gene comprising SEQ ID NO. 5 and about 480 bp of heavy chain cDNA gene comprising SEQ ID NO. 6, respectively.

From the said monoclonal antibody light and heavy chains, the CDR (complementarity determining region) residues were detected. As a result, it is identified that the CDR residues of the light chain exist at the positions of 24–40, 56–62, and 95–102 representing the peptides of SEQ ID Nos. 9, 10, and 11, respectively. Further, it is found that the CDR residues of the heavy chain exist at the positions of 31–35, 50–66, and 99–111 representing the peptides of SEQ ID Nos. 12, 13, and 14, respectively.

Accordingly, the present invention includes, within its scope, a cDNA encoding a light chain variable region of a monoclonal antibody against the HBV S-surface antigen, the said light chain variable region comprising the peptides of SEQ ID Nos. 9, 10, and 11. Further, the present invention includes a cDNA wherein the light chain variable region has the amino acid sequence of SEQ ID NO. 7, and preferably, a cDNA comprising the nucleotide sequence of SEQ ID NO. 5.

And also, the present invention includes, within its scope, a cDNA encoding a heavy chain variable region of a monoclonal antibody against the HBV S-surface antigen, the said heavy chain variable region comprising the peptides of SEQ ID Nos. 12, 13, and 14. Further, the present invention includes a cDNA wherein the heavy chain variable region has the amino acid sequence of SEQ ID NO. 8, and preferably, a cDNA comprising the nucleotide sequence of SEQ ID NO. 6.

The above cDNA genes encoding the light or heavy chain variable region of a monoclonal antibody may be inserted into plasmid vector such as pCRII (Invitrogen Co. USA) to give recombinant vectors. Accordingly, the present invention includes, within its scope, a recombinant vector pCRC6Lv comprising the above cDNA encoding a light chain variable region and a recombinant vector pCRC6Hv comprising the above cDNA encoding a heavy chain variable region.

Further, microorganisms, such as E. coli, may be transformed with the above recombinant vectors, pCRC6Lv and/or pCRC6Hv, to obtain transformants. Accordingly, the present invention includes a transformant E. coli DH5a/pCRC6Lv (Accession No. KCTC 10239BP) and a transformant E. coli DH5a/pCRC6Hv (Accession No. KCTC 10238BP) which are transformed with a recombinant vector pCRC6Lv and pCRC6Hv, respectively. The transformant E. coli DH5a/pCRC6Lv (KCTC 10239BP) and transformant E. coli DH5a/pCRC6Hv (KCTC 10238BP) have been deposited in International Depositary authority: Korean Culture for Type Cultures (KCTC). #52. Oun-dong. Yusong-ku, Tacjon 305–333, Republic of Korea, on May 6, 2002, respectively, under Budapest Treaty.

Recombinant vectors may be recovered from the above transformants using known methods (J. Sambrook et al., Molecular cloning, Vol. 1, 1.25–1.28). For example, the cell membrane of a transformant may be weakened with solution 1 (50 mM glucose, 25 mM Tris HCl, and 10 mM EDTA). With solution 2 (0.2N NaOH and 1% SDS) the cell membrane may be destroyed and proteins and chromosomes may be denatured. The ingredients other than recombinant vectors may be aggregated with solution 3 (5M potassium acetate and acetic acid) and then centrifuged. The obtained recombinant vector layer may be precipitated with ethanol to recover recombinant vectors.

The present invention includes, within its scope, a monoclonal antibody variable region, which consists of a light chain comprising the peptides of SEQ ID Nos. 9, 10, and 11 and a heavy chain comprising the peptides of SEQ ID Nos. 12, 13, and 14. Further, preferable is a monoclonal antibody variable region, wherein the light chain variable region has the amino acid sequence of SEQ ID NO. 7 and the heavy chain variable region has the amino acid sequence of SEQ ID NO. 8.

From the above cDNA genes encoding a monoclonal antibody variable region according to the present invention, a humanized monoclonal antibody against HBV may be obtained by fusing the CDR region where S-surface antigen binds directly (i.e., in case of the light chain, the gene encoding the peptides of SEQ ID Nos. 9, 10, and 11; and in case of the heavy chain, the gene encoding the peptides of SEQ ID Nos. 12, 13, and 14) to a human antibody gene, or by substituting a human antibody variable region with a gene encoding the monoclonal antibody variable region according to the present invention.

As mentioned above, the gene encoding the monoclonal antibody variable region according to the present invention is specifically effective in the recognition of HBV S-surface antigen, especially determinant a, which has the highest expression ratio in the HBV surface antigens. Therefore, the gene according to the present invention may be used to manufacture monoclonal antibodies which may be widely applied to various types of HBV surface antigens, such as adr, adw, ayr and ayw, to neutralize and/or remove HBV.

BEST MODE FOR CARRYING OUT THE INVENTION

The present invention will now be further illustrated in detail by, but is by no means limited to, the following Examples.

EXAMPLE 1

RNA Isolation From the Cell Line (mC6-9-1) and its cDNA Synthesis

After $1\times10^8$ of mC6-9-1 cells were added to 10 ml of 4M guanidinium thiocyanate to disrupt the cells, 8 ml of acidic phenol solution was added thereto. The mixture was centrifuged (10,000 rpm, 10 minutes) to extract the RNA. To 5 μg of the extracted RNA, were added 0.5 ng of oligo d(T), 0.5 unit of RNase inhibitor and 100 unit of moloney murine leukemia virus reverse transcriptase (M-MLV). The resulting mixture was reacted at 37° C. for 1 hour to synthesize cDNA.

Using 2 μg of the synthesized cDNA as a template; in case of the light chain, the DNA oligomers of SEQ ID Nos. 1 and 2 as primers; and in case of the heavy chain, the DNA oligomers of SEQ ID Nos. 3 and 4 as primers, polymerase chain reaction (PCR) was performed with the use of an AmpliTaq polymerase (Perkin-Ehuer Biosystem Co., USA). In the first step of the PCR, the reaction was repeated 30 cycles in the reaction conditions of 1.5 minute at 94° C., 2 minutes at 55° C., and 3 minutes at 72° C. In the second step, the reaction was performed 1 cycle in the condition of 1.5 minute at 94° C., 2 minutes at 55° C. and 10 minutes at 72° C.

1.5% Agarose gel electrophoresis was preformed using amplified PCR product. After stained with 100 ml of 0.5 μg/ml ethiditum bromide solution for 20 minutes, the amplified gene products appeared about 480 bp in case of the heavy chain and about 440 bp in case of the light chain compared to 100 bp of standard DNA ladder (Lifetechnology Co. USA).

EXAMPLE 2 cDNA Cloning

After removing impurities by adding 200 μl of phenol and 200 μl of chloroform to the 440 bp gene fragment (the light chain gene fragment), which was recovered using a dialysis membrane (Spectrum Co. USA) after performing 1.5% agarose gel electrophoresis in Example 1, 2.5 ml of ethanol was added to purify the gene fragment. Purified gene fragment was subcloned into a pCRII vector (Invitrogen Co., USA) and E. coli DH5$^a$ (Lifetechnology Co., USA) was transformed therewith to give a transformant (Cohen, S. N. et al., Proc. Nat. Acad. Sci. 69, 2110, 1972). The obtained transformant was cultured overnight in the LB medium containing 100 μg/ml of ampicillin and, subsequently, processed to give a plasmid. Then, the plasmid was cut with a restriction enzyme EcoRI (Biolab Co., USA) to give clones CS-2, CS-4, and CS-5 in which the above 440 bp of gene fragment was inserted.

The same procedures were performed with the 480 bp gene fragment (the heavy chain gene fragment) to give a recombinant vector, with which E. coli DH5$^a$ (Lifetechnology Co., USA) was transformed to obtain a transformant. The transformant was cultured overnight in the LB medium containing 100 μg/ml of ampicillin and subsequently, processed to give a plasmid. Then the plasmid was cut with a restriction enzyme EcoRI (Biolab Co., USA) to give clones CS-6, CS-7, and CS-8 in which the above 480 bp of gene fragment was inserted.

60 μl of polyethylene glycol solution (20% polyethylene glycol and 2.5M NaCl) was added to 100 μg/ml of each plasmid solution obtained from the above clones and then centrifuged. 100 μl of distilled water was added to the resulting precipitate, extracted twice with 50 μl of phenol solution, and 200 μl of ethanol was used to purify plasmids.

5 μl of 2N sodium hydroxide and 10 μl of 10 mM EDTA were added to 50 μl of the solution containing 2 μg of the purified plasmid. Then, the mixture was reacted at 37° C. for 30 minutes. To the reaction mixture, 1 pmol of M13 and T7 primers were added, respectively. The whole mixture was reacted 2 minutes at 65° C., and then allowed to stand to room temperature. The nucleotide sequences of each clone were analyzed using DNA sequence version II kit (United States Biochemical Co., USA).

As a result, the nucleotide sequences of three light chain clones (CS-2, CS-4, and CS-5) were identical. The plasmid vectors obtained from these clones were named pCRC6Lv. And the transformants with pCRC6Lv plasmid vectors were named E. coli DH5$^a$/pCRC6Lv which was deposited under the Budapest Treaty in Korean Collection for Type Cultures (KCTC) in Korea Research Institute of Biosci. & Biotech on May 3, 2001 (KCTC 10239BP).

Further, the nucleotide sequences of three heavy chain clones (CS-6, CS-7, and CS-8) were identical. The plasmid vectors obtained from these clones were named pCRC6Hv. And the transformants with pCRC6Hv plasmid vectors were named E. Coli DH5$^a$/pCRC6Hv which was deposited under the Budapest Treaty in Korean Collection for Type Cultures (KCTC) in Korea Research Institute of Biosci. & Biotech on May 3, 2001 (KCTC 10238BP).

EXAMPLE 3

Nucleotide Sequence Analysis of the cDNA

As a result of analysis on the variable region amino acid sequence (Harris. L. et at., Protein Sci. 4, 306–310, 1995.; Kabat. E. A. et al., Sequence of proteins of immunological interest.5th Ed., 1991.; Williams A. F. et al., Annu. Rev. Immunol. 6, 381–406, 1988) of the monoclonal antibody obtained from the cell line mC6-9-1, it was identified that the heavy chain belongs to II(B) subgroup and the light chain belongs to k1 series.

Among the variable regions, the antigen-recognition CDR residues of the heavy chain were at the positions of 31–35 (CDR1), 50–66 (CDR2), and 99–111 (CDR3) and those of the light chain were of 24–40 (CDR1), 56–62 (CDR2), and 95–102 (CDR3).

EXAMPLE 4

Binding Affinity of the Monoclonal Antibody Obtained from the Hybridoma Cell Line mC6-9-1

$2.0 \times 10^{-11}$M of the monoclonal antibody obtained from the cell line mC6-9-1 was added to the solution of the HBV S-surface antigen (International Enzymes Inc., USA) at various concentrations ($1.0 \times 10^{-6} \sim 1.0 \times 10^{-12}$M) and then the mixture was reacted at room temperature for 3 hours.

100 μl of each mixture was added to 96-well immulon plates (Dinatech Co. USA) where 0.1 μg of above S-surface antigen was pre-coated. The mixture was incubated 2 hours at 37° C. and the supernatant solution was removed 200 μl of 0.5% casein-phosphate buffered saline was added to each well and further incubated 1 hour at 37° C. 100 μl of the diluted (×1,000) goat anti-mouse polyclonal antibody to which horseradish peroxidase was conjugated (Sigma Co., USA) was added, and its optical density was measured using ELISA reader (Dinatech Co., USA).

The monoclonal antibody obtained from the cell line mC6-9-1 has high binding affinity of $0.24 \times 10^{-9}$ $M^{-1}$. The term of binding affinity means that the reciprocal of the antigen concentration at which 50% of monoclonal antibody binding is inhibited (Friguet B. et al., J. of Immunological Method, 77, 305–319, 1985)

While the invention has been described with respect to the specific embodiments, it should be recognized that various modifications and changes may be made by those skilled in the art to the invention which also fall within the scope of the invention as defined as the appended claims.

---

What is claimed is:

1. A cDNA encoding a light chain variable region of a monoclonal antibody against S-surface antigen of hepatitis B virus, wherein said light chain variable region comprises the CDRL1, CDRL2, and CDRL3 peptides of SEQ ID Nos. 9, 10, and 11, respectively.

2. The cDNA according to claim 1, wherein the light chain variable region has the amino acid sequence of SEQ ID NO. 7.

3. The cDNA according to claim 2, which comprises the nucleotide sequence of SEQ ID NO. 5.

4. A cDNA encoding a heavy chain variable region of a monoclonal antibody against S-surface antigen of hepatitis B virus, wherein said heavy chain variable region comprises the CDRH1, CDRH2 and CDRH3 peptides of SEQ ID Nos. 12, 13, and 14, respectively.

5. The cDNA according to claim 4, wherein the heavy chain variable region has the amino acid sequence of SEQ ID NO. 8.

6. The cDNA according to claim 5, which comprises the nucleotide sequence of SEQ ID NO. 6.

7. A recombinant vector pCRC6Lv comprising the cDNA of claim 1.

8. A recombinant vector pCRC6Hv comprising the cDNA of claim 4.

9. A transformant E. coli DH5a/pCRC6Lv (KCTC 10239BP), which is transformed with the recombinant vector pCRC6Lv of claim 7.

10. A transformant E. coli DH5a/pCRC6Hv (KCTC 10238BP), which is transformed with the recombinant vector pCRC6Hv of claim 8.

* * * * *